United States Patent [19]

Manimaran et al.

[11] Patent Number: 4,968,837
[45] Date of Patent: Nov. 6, 1990

[54] RESOLUTION OF RACEMIC MIXTURES

[75] Inventors: Thanikavelu Manimaran; Fred J. Impastato, both of Baton Rouge, La.

[73] Assignee: Ethyl Corporation, Richmond, Va.

[21] Appl. No.: 386,277

[22] Filed: Jul. 28, 1989

[51] Int. Cl.$^5$ .............................................. C07B 57/00
[52] U.S. Cl. ..................................... 562/470; 564/304
[58] Field of Search ......................... 564/304; 562/470

[56] References Cited

U.S. PATENT DOCUMENTS

| | | | |
|---|---|---|---|
| 1,927,961 | 9/1933 | Stolz et al. | 564/304 |
| 3,198,834 | 8/1965 | Beregi et al. | 564/304 X |
| 3,312,733 | 4/1967 | Howe | 564/304 X |
| 4,410,519 | 10/1983 | Seiler et al. | 564/167 X |
| 4,564,628 | 1/1986 | Horn | 514/438 |
| 4,657,925 | 4/1987 | Horn | 514/438 |

OTHER PUBLICATIONS

McDermed et al., *Journal of Medicinal Chemistry*, vol. 19, No. 4, pp. 547–549, (1976).
Leigh, *Chemistry and Industry*, p. 36, Jan. 1, 1977.
Brunner et al., *Angew. Chem. Int. Ed. Engl.*, vol. 18, No. 8, pp. 620–621, (1979).
Howe et al., *J. Org. Chem.*, vol. 50, pp. 4508–4514, (1985).
Seiler et al., *Journal of Medicinal Chemistry*, vol. 29, pp. 912–917, (1986).
Gerding et al., *Journal of High Resolution Chromatography & Chromatography Communications*, vol. 10, pp. 523–525, Sep. 1987.

*Primary Examiner*—Werren B. Lone
*Assistant Examiner*—Vera C. Clarke
*Attorney, Agent, or Firm*—Patricia J. Hogan; Richard J. Hammond

[57] ABSTRACT

Racemic 2-(N-propylamino)-5-methoxytetralin is resolved by treating it with a chiral diaroyltartaric acid in an organic solvent at an elevated temperature to form a salt of the amine and chiral diaroyltartaric acid which is soluble in the solvent at the elevated temperature, cooling to precipitate the salt, isolating it, and converting it to the free amine. The product is useful as an intermediate in the synthesis of optionally-active pharmaceutical, such as N-0437.

9 Claims, No Drawings

RESOLUTION OF RACEMIC MIXTURES

BACKGROUND OF INVENTION

This invention relates to the resolution of racemic mixtures and more particularly to a process for resolving racemic 2-(N-propylamino)-5-methoxytetralin.

BACKGROUND

As disclosed in U.S. Pat. Nos. 4,410,529 (Seiler et al.), 4,564,628 (Horn-I), and 4,657,925 (Horn-II), it is known that 2-(N-propylamino)-5-methoxytetralin is useful as an intermediate in the preparation of dopamine receptor agonists, such as 2-(N-propyl-N-2-thienylethylamino)-5-hydroxytetralin hydrochloride (also known as N-0437), which can be utilized in the treatment of parkinsonism, etc. Horn-II teaches that racemic 2-(N-propylamino)-5-methoxytetralin can be resolved into its enantiomers before being converted to N-0437 and that the product formed from the (−)-enantiomer has a pharmacological activity which is 140 times the activity of the product formed from the (+)-enantiomer.

Since it is desirable to be able to provide N-0437 and other such pharmaceuticals as (+)- or (−)-enantiomers, various techniques have been used to resolve them or intermediates used in preparing them. For example, (1) Gerding et al., *Journal of High Resolution Chromatography & Chromatography Communications,* Vol. 10, September 1987, pp. 523–525, teach that N-0437 has been resolved by (a) derivatization with (+)-glucuronic acid followed by separation in a non-chiral chromatographic system or (b) crystallization with the chiral phosphoric acids of ten Hoeve et al., *J. Org. Chem.*, 1985, Vol. 50, pp. 4508–4514, i.e., with certain rather exotic compounds, such as 4,-(2-chlorophenyl)-5,5-dimethyl-2-hydroxy-1,3,2-dioxaphosphorinane 2-oxide, which are expensive and time-consuming to synthesize and resolve; and (2) Seiler et al., *J. Med. Chem.*, 1986, Vol. 29, pp. 912–917, disclose that (−)-2-(N-propylamino)-5-methoxytetralin can be obtained by the propylation and subsequent debenzylation of (−)-2-(N-benzylamino)-5-methoxytetralin, a compound which McDermed et al., *J. Med. Chem.*, 1976, Vol. 19, No. 4, pp. 547–549, teach to be prepared by reacting 5-methoxytetralone with benzylamine and resolving the resultant racemic 2-(N-benzylamino)-5-methoxytetralin with (−)-mandelic acid.

None of these known resolution techniques is attractive in the preparation of N-0437 and other such pharmaceuticals, so it would be desirable to find a more efficient and less expensive way to resolve the pharmaceuticals or the 2-(N-propylamino)-5methoxytetralin that can be used in preparing them. However, many common resolving agents, such as the (+)- and (−)-camphor sulfonic acids, the (+)- and (−)-mandelic acids, and (−)-malic acid, have been found to be unsatisfactory for use in resolving either N-0437 or 2-(N-propylamino)-5-methoxytetralin.

Leigh, *Chemistry and Industry,* 1 January 1977, p. 36, teaches that (+)-tartaric acid and its dibenzoyl and ditoluoyl derivatives are among the more common chiral acids used as resolving agents for bases. Brunner et al., *Angew. Chem. Int. Ed. Engl.,* Vol. 18, No. 8, 1979, pp. 620–621, show that dibenzoyl-(−)-tartaric acid is also a known resolving agent.

SUMMARY OF INVENTION

An object of this invention is to provide a novel process for resolving racemic 2-(N-propylamino)-5-methoxytetralin.

Another object is to provide such a process which is efficient and economical.

A further object is to provide such a process which can be integrated into an efficient, economical process for preparing N-0437 and similar pharmaceuticals.

These and other objects are attained by treating racemic 2-(N-propylamino)-5-methoxytetralin with a chiral diaroyltartaric acid in an organic solvent at an elevated temperature to form a salt of the amine and diaroyltartaric acid which is soluble in the solvent at the elevated temperature, cooling to precipitate the salt, and isolating it.

DETAILED DESCRIPTION

The racemic 2-(N-propylamino)-5-methoxytetralin which is resolved in the practice of the invention is the free amine. Thus, when it has been prepared in the form of the hydrochloride, it is neutralized with a suitable base, such as sodium hydroxide, before being treated with the diaroyltartaric acid resolving agent.

The chiral diaroyltartaric acid employed is a (+)- or (−)-enantiomer, depending on the 2-(N-propylamino)-5-methoxytetralin enantioner desired. For reasons of cost and availability, the preferred resolving agents are dibenzoyl-(−)-tartaric acid and dibenzoyl-(+)-tartaric acid. However, other diaroyl-(−)-tartaric acids, such as ditoluoyl-(−)-tartaric acid, and other diaroyl-(+)-tartaric acids, such as ditoluoyl-(+)-tartaric acid, are also utilizable. The amount of resolving agent employed is generally about one mol per mol of racemic 2-(N-propylamino)-5-methoxytetralin.

The organic solvent used in the process may be any such solvent in which the salt formed from the amine and the chiral diaroyltartaric acid is soluble at an elevated temperature but insoluble at ambient temperatures. Exemplary of suitable solvents are methanol, ethanol, isopropanol, n-butanol, acetone, methyl ethyl ketone, ethyl acetate, t-butyl acetate, methylene chloride, and mixtures thereof.

The elevated temperature employed for the salt formation may be any such temperature at which the salt is soluble, but it is usually a temperature in the range of about 50°–100° C. When the solvent is ethyl acetate, the preferred elevated temperature is 65°–70° C.

The resolution is accomplished by heating a solution of the resolving agent in an appropriate solvent to the elevated temperature desired, adding a solution of the amine in the same or a different solvent to the resolving agent solution while stirring and continuing to maintain the solution at the elevated temperature, allowing the reaction mixture to cool to room temperature while continuing to stir it, and isolating the precipitated salt of the amine and chiral diaroyltartaric acid.

Isolation of the salt is accomplished by conventional means. Thus, the precipitated salt is separated from the reaction mixture by any suitable means, e.g., filtration, and is usually then washed, e.g., with acetone, and subsequently redissolved and reprecipitated at least once to provide a purer product.

After the salt has been isolated, it can be converted to the free chiral amine by conventional means, e.g., by reacting it with a base such as an amine or an alkali or alkaline earth metal hydroxide, e.g., sodium hydroxide, and the resultant 2-(N-propylamino)-5-methoxytetralin enantiomer can then be converted to an enantiomer of N-0437 or other such pharmaceutical by known techniques, such as those taught by Seiler et al. and Horn-I, the teachings of both of which are incorporated herein in toto by reference.

The invention is advantageous as an efficient, economical process for resolving racemic 2-(N-propylamino)-5-methoxytetralin to provide a product which can be used as an intermediate in the preparation of the enantiomers of known pharmaceuticals.

The following examples are given to illustrate the invention and are not intended as a limitation thereof.

EXAMPLE I

Part A

A suitable reaction vessel was charged with a mixture of 1L of 5% sodium hydroxide and 500 mL of ether. The mixture was cooled with an ice-water bath, and 200 g (0.78 mol) of racemic 2-(N-propylamino)-5-methoxytetralin hydrochloride was added in small portions with stirring. Stirring was continued for one hour, after which the layers were separated. The lower, aqueous layer was extracted with three 300-mL portions of ether, and the ether layers were then combined and dried by adding 50 g of anhydrous magnesium sulfate, stirring for five minutes,, and filtering. The filtrate was concentrated in vacuo to give 172 g of residue containing crude 2-(N-propylamino)-5-methoxytetralin free amine, which was then dissolved in 200 mL of ethyl acetate.

Part B

A resolving agent solution was obtained by adding 290 g (0.77 mol) of dibenzoyl-(−)-tartaric acid monohydrate to 1L of ethyl acetate with stirring, and the resulting solution was heated to 65°–70° C. The free amine solution of Part A was then added dropwise to the hot resolving agent solution with stirring and continued heating. After completion of the addition of the amine solution, the reaction mixture was allowed to cool to room temperature overnight with stirring to precipitate the dibenzoyl-(−)tartaric acid salt of 2-(N-propylamino)-5-methoxytetralin. The precipitated salt was collected by filtration, washed with 100 mL of acetone, dissolved in 1500 mL of hot ethyl acetate, and then reprecipitated by allowing the solution to cool overnight with stirring. The resulting crystalline salt was collected by filtration and then redissolved and reprecipitated to provide 124 g of crystalline dibenzoyl-(−)-tartaric acid salt of (−)-2-(N-propylamino)-5-methoxytetralin having a specific rotation in the range of −103° to −109°.

Part C

A stirred mixture of 200 mL of 10% sodium hydroxide and 200 mL of ether was cooled to 0°–5° C. in an ice-water bath, the product of Part B was added, and the reaction mixture was stirred for 30 minutes, after which the layers were separated. The lower, aqueous layer was extracted with three 200-mL portions of ether, and the ether layers were then combined and dried by adding 50 g of anhydrous magnesium sulfate, stirring for five minutes, and filtering. The resulting solution was concentrated in vacuo to give a residue containing (−)-2-(N-propylamino)-5-methoxytetralin free amine having a specific rotation of about −65°.

EXAMPLE II

Part A

The filtrates from Example I, Part B, were combined, the solvent was stripped off, and the residue was treated with 1L of 10% sodium hydroxide solution and extracted with four 300 mL portions of ether. The ether layers were combined and dried by adding 50 g of anhydrous magnesium sulfate, stirring for five minutes, and filtering. The filtrate was concentrated in vacuo to give crude 2-(N-propylamino)-5-methoxytetralin free amine.

Part B

A solution of 87.5 g (0.4 mol) of the free amine of Part A in 250 mL of acetone was added in drops to a hot (∼60° C.) stirred solution of 150 g (0.4 mol) of dibenzoyl-(+)-tartaric acid in 1L of acetone. The reaction mixture was allowed to cool to room temperature by stirring overnight. The precipitated dibenzoyl(+)-tartaric acid salt of 2-(N-propylamino)-5-methoxytetralin was collected by filtration, washed with 100 mL of acetone, dissolved in 2.5L of hot ethanol, and then reprecipitated by allowing the solution to cool overnight with stirring. The resulting salt was collected by filtration and then redissolved and reprecipitated to provide 92 g of crystalline dibenzoyl-(+)-tartaric acid salt of (+)-2-(N-propylamino)-5-methoxytetralin having a specific rotation in the range of +105° to +109°.

Part C (+)-2-(N-propylamino)-5-methoxytetralin was liberated from the product salt of Part C as in Example I, Part C. The free amine had a specific rotation of about +65°.

The preceding examples demonstrate that chiral diaroyltartaric acids are effective in resolving racemic 2-(N-propylamino)amino)-5-methoxytetralin. The following examples show that this result could not have been expected in view of the failure of the same common resolving agents to resolve N-0437, a derivative of 2-(N-propylamino)-5-methoxytetralin, and in view of the failure of other common resolving agents to resolve racemic 2-(N-propylamino)-5-methoxytetralin.

COMPARATIVE EXAMPLE A

A solution of 3.3 g (0.01 mol) of N-0437 free amine in 15 mL of acetone was added to a hot solution of 3.76 g (0.01 mol) of dibenzoyl-(−)-tartaric acid in 25 mL of acetone. The reaction mixture was allowed to cool to room temperature by stirring overnight. No solid salt was precipitated, and only a viscous oil was obtained by keeping it for several days.

COMPARATIVE EXAMPLE B

A solution of 11 g (0.05 mol) of 2-(N-propylamino)-5-methoxytetralin in 25 mL of acetone was added in drops to a hot solution of 7.6 g (0.05 mol) of (−)-mandelic acid in 100 mL of acetone. The mixture was allowed to cool to room temperature by stirring overnight. The precipitated (−)-mandelic acid salt was collected by filtration and washed with 20 mL of ether. The specific rotation of the salt (11.8 g) was −42°. This salt was recrystallized three times in acetone to provide 4.35 g of (−)-mandelic acid salt of 2-(N-propylamino)-5-methoxytetralin. The specific rotation of the salt did not change after the recrystallizations.

The salt was stirred with 10 mL of 10% sodium hydroxide solution and extracted with three 15 mL portions of ether. The ether layers were combined, dried over anhydrous magnesium sulfate, and filtered. The filtrate was concentrated in vacuo to give 2-(N-propylamino)-5-methoxytetralin which was found to be racemic by specific rotation measurements.

COMPARATIVE EXAMPLE C

A solution of 6.58 g (0.03 mol) of 2-(N-propylamino)-5-methoxytetralin in 25 mL of ethanol was mixed with a solution of 6.97 g (0.03 mol) of (−)-camphorsulfonic acid in 25 mL of ethanol and left aside for several days. A viscous residue was obtained.

Methanol, acetone, ethyl acetate, methylene chloride, and mixtures of these solvents with ether were tried as solvent systems for the salt formation. However, no solid salt could be obtained.

It is obvious that many variations may be made in the products and processes set forth above without departing from the spirit and scope of this invention.

What is claimed is:

1. A process for resolving racemic 2-(N-propylamino)-5-methoxytetralin which comprises treating it with a chiral diaroyltartaric acid in an organic solvent at an elevated temperature to form a salt of the amine and chiral diaroyltartaric acid which is soluble in the solvent at the elevated temperature, cooling to precipitate the salt, and isolating it.

2. The process of claim 1 wherein the chiral diaroyltartaric acid is dibenzoyl-(−)-tartaric acid.

3. The process of claim 1 wherein the chiral diaroyltartaric acid is dibenzoyl-(+)-tartaric acid.

4. The process of claim 1 wherein the solvent is ethyl acetate.

5. The process of claim 1 wherein the elevated temperature is in the range of about 50°–100° C.

6. The process of claim 5 wherein the temperature is 65°–70° C.

7. The process of claim 1 wherein the precipitated salt is separated from the reaction mixture by filtration and subsequently redissolved and reprecipitated at least once.

8. The process of claim 1 wherein the precipitated salt, after isolation from the reaction mixture, is reacted with a base to convert it to a 2-(N-propylamino)-5-methoxytetralin enantiomer.

9. The process of claim 1 wherein racemic 2-(N-propylamino)-5-methoxytetralin is treated with a substantially equimolar amount of dibenzoyl-(−)-tartaric acid at 65°–70° to form a salt of the amine and dibenzoyl-(−)-tartaric acid, the salt is precipitated by cooling the reaction mixture, the precipitated salt is separated from the reaction mixture by filtration and subsequently redissolved and reprecipitated at least once, and the isolated precipitated salt is reacted with sodium hydroxide to convert it to (−)-2-(N-propylamino)-5-methoxytetralin.

* * * * *